(12) United States Patent
    Piccagli

(10) Patent No.: US 10,299,823 B2
(45) Date of Patent: May 28, 2019

(54) SCORING BALLOON CATHETER

(71) Applicant: Medtronic Vascular, Inc., Santa Rosa, CA (US)

(72) Inventor: Francesco Piccagli, Brescia (IT)

(73) Assignee: Medtronic Vascular, Inc., Santa Rosa, CA (US)

( * ) Notice: Subject to any disclaimer, the term of this patent is extended or adjusted under 35 U.S.C. 154(b) by 688 days.

(21) Appl. No.: 14/887,986

(22) Filed: Oct. 20, 2015

(65) Prior Publication Data

US 2017/0105758 A1    Apr. 20, 2017

(51) Int. Cl.
    *A61B 17/22*    (2006.01)
    *A61B 17/3207*   (2006.01)

(52) U.S. Cl.
    CPC .. *A61B 17/320725* (2013.01); *A61B 17/3207* (2013.01); *A61B 2017/22051* (2013.01); *A61B 2017/22061* (2013.01)

(58) Field of Classification Search
    CPC ............ A61M 25/104; A61M 25/1002; A61M 25/1011; A61M 25/10; A61M 2025/1086; A61M 2025/109; A61M 2025/1074; A61M 2025/1013; A61M 2025/1072; A61M 2025/1079; A61M 2025/1088; A61M 2029/025; A61M 29/02; A61M 17/22; A61M 17/32075; A61M 2017/22001; A61B 17/320725; A61B 17/22012; A61B 17/50; A61B 2017/32075; A61B 2017/22051; A61F 2002/9583; A61F 2/958
    See application file for complete search history.

(56) References Cited

U.S. PATENT DOCUMENTS

| | | | | |
|---|---|---|---|---|
| 2005/0021071 | A1* | 1/2005 | Konstantino | A61B 17/320725 606/194 |
| 2005/0240212 | A1* | 10/2005 | McAuley | A61M 25/10 606/194 |
| 2009/0192537 | A1* | 7/2009 | O'Brien | A61B 17/320725 606/159 |
| 2011/0152683 | A1* | 6/2011 | Gerrans | A61B 17/22012 600/435 |

\* cited by examiner

*Primary Examiner* — Robert A Lynch
*Assistant Examiner* — Mohamed G Gabr

(57) ABSTRACT

A scoring balloon catheter includes a scoring balloon, a distal control balloon positioned distal of the scoring balloon, a proximal control balloon positioned proximal of the scoring balloon, and a scoring element coupled to the proximal and distal control balloons. The scoring balloon is configured to expand radially and contact the scoring element.

19 Claims, 18 Drawing Sheets

SCORING BALLOON CATHETER

FIELD OF THE INVENTION

The present invention relates to systems and methods for catheters for use in administering treatments to relieve a stenotic region, or to widen a constricted blood flow, bodily lumen, or tubular lumen, such as the coronary artery, as well as other blood vessels.

BACKGROUND

Arterial blockages, which are also called stenoses, lesions, stenotic lesions, etc., are typically caused by the build-up of atherosclerotic plaque on the inside wall of an artery. In some cases, several such stenoses may occur contiguously within a single artery. This can result in partial, or even complete, blockage of the artery. Several methods for treating stenoses have been developed. One such treatment option is traditional coronary arterial bypass surgery. Traditional bypass surgery inflicts significant patient trauma and discomfort, requires extensive recuperation times, and may result in life-threatening complications.

To address these concerns, percutaneous transluminal angioplasty (PTA) has been developed and has become a widely accepted therapeutic alternative to bypass surgery for many patients. Percutaneous transluminal angioplasty increases the lumen by radial expansion, such as with a balloon. When considering angioplasty as a method of treating the stenotic region, the morphology of the lesion is critical in determining whether a balloon catheter can be used and whether the vessel will adequately dilate. If the stenosis is hard, or has calcified, first, or simultaneously incising the stenotic material may increase efficacy of the dilation. Angioplasty balloons have thus been made and equipped with cutting edges attached to the surface of the balloon. These cutting edges are intended to incise the stenosis during the dilation procedure.

There is a need for a balloon catheter with improved control of the scoring element expansion, increased position control within the lesion, a more homogeneous scoring effect along the entire length of the scoring balloon, and better control of the alignment of the scoring element in relation to the longitudinal axis of the treated vessel.

SUMMARY OF THE INVENTION

Embodiments hereof relate to a scoring balloon catheter for treating a site within a body lumen via percutaneous transluminal angioplasty (PTA). The scoring balloon catheter includes a scoring balloon, a distal control balloon distal of the scoring balloon, a proximal control balloon proximal of the scoring balloon, and a scoring element. The scoring element is coupled at its proximal end to the proximal control balloon and at its distal end to the distal control balloon. The proximal and distal control balloons are configured to expand radially outward to contact the body lumen. The scoring balloon is configured to expand radially outward to contact the scoring element. The proximal and distal control balloons may be compliant. The scoring balloon may be semi-compliant or non-compliant. The proximal and distal control balloons may be inflated/uninflated together or independently of each other. The scoring balloon may be inflated/uninflated independently of the proximal and distal control balloons.

Embodiments hereof are also related to a method for scoring a lesion within a patient's vasculature. A balloon catheter is delivered through the patient's vasculature to the lesion. The balloon catheter includes a scoring balloon, a distal control balloon distal of the scoring balloon, and a proximal control balloon proximal of the scoring balloon. A scoring element is disposed between, and coupled to the proximal and distal control balloons. The balloon catheter is positioned such that the scoring balloon is within the lesion. Next, the proximal and distal control balloons are inflated, and the scoring element becomes taut. Next, the scoring balloon is inflated such that the scoring balloon contacts the scoring element and forces the scoring element radially outward relative to the longitudinal axis of the balloon catheter such that the scoring element engages the lesion.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION

Specific embodiments of the present invention are now described with reference to the figures, wherein like reference numbers indicate identical or functionally similar elements. The terms "distal" and "proximal" when used in the following description to refer to a catheter or delivery system are with respect to a position or direction relative to the treating clinician. Thus, "distal" and "distally" refer to positions distant from, or in a direction away from, the clinician and "proximal" and "proximally" refer to positions near or in a direction toward the clinician.

The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

Figure 1:
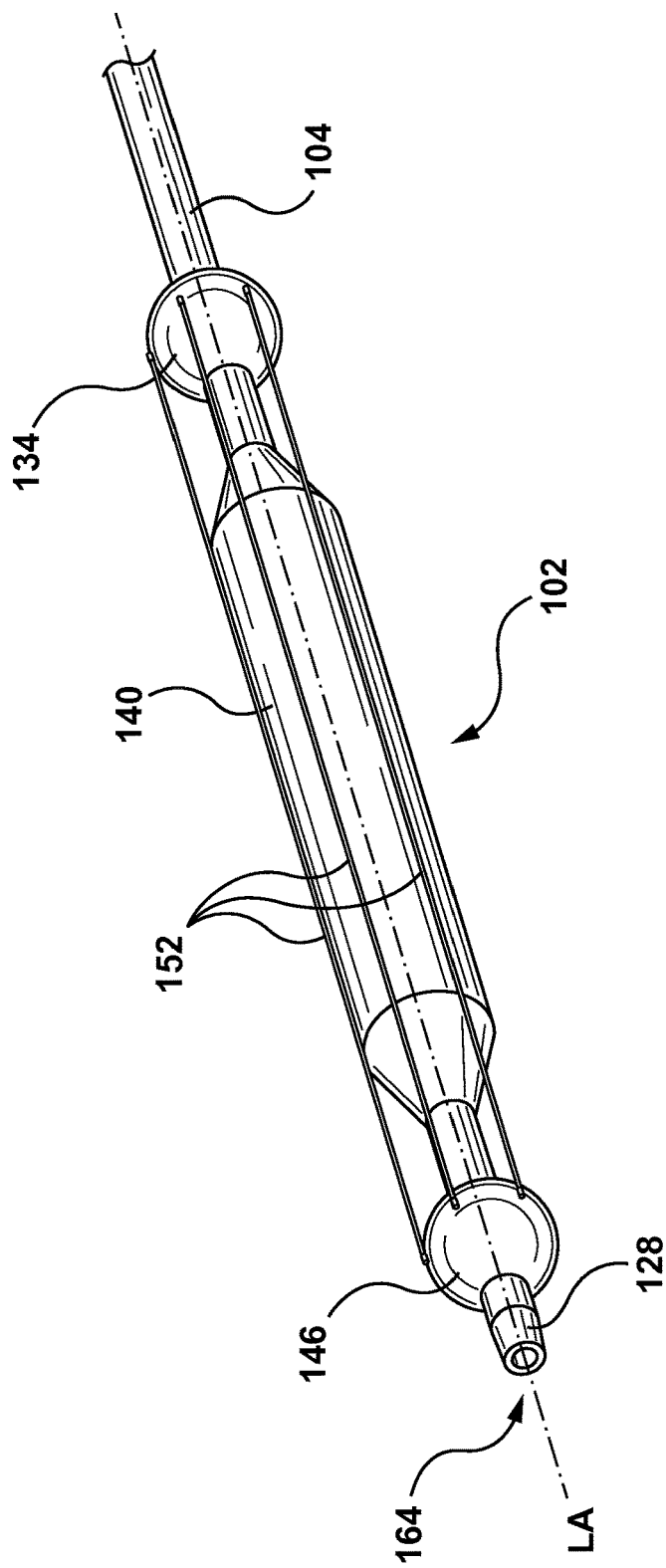
FIG. 1 is a perspective view of an embodiment of a scoring balloon catheter of the current disclosure with the proximal and distal control balloons and the scoring balloon inflated.
Figure 2:
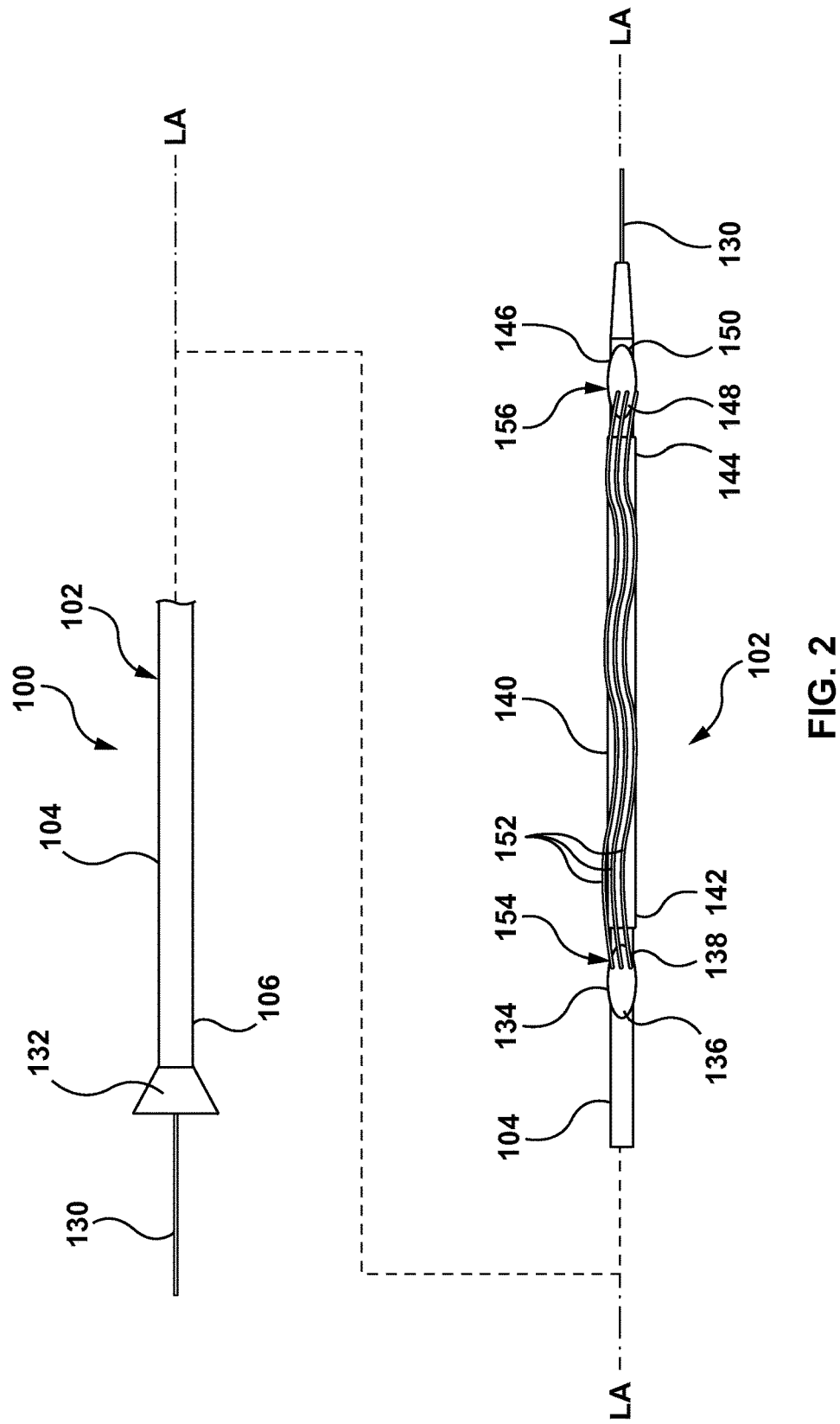
FIG. 2 is a side view of an embodiment of a catheter system with the scoring balloon catheter of FIG. 1 with the proximal and distal control balloons and the scoring balloon not inflated.

With the above understanding in mind, one non-limiting example of a catheter system 100 is shown in FIGS. 1-7. Catheter system 100 includes a scoring balloon catheter 102, a hub 132, and a guidewire 130, as shown in FIG. 2 and explained in more detail below. The scoring balloon catheter 102 includes a catheter shaft 104, a proximal control balloon 134, a scoring balloon 140, a distal control balloon 146, and a plurality of scoring elements 152.

Catheter shaft 104 may be any standard construction PTA catheter shaft, such as, but not limited to, multi-lumen or coaxial construction catheter shafts. Catheter shaft 104 includes a guidewire lumen 164 and a longitudinal axis LA. Guidewire lumen 164 is disposed through the entirety of scoring balloon catheter 102, and extends along longitudinal axis LA of scoring balloon catheter 102. A guidewire 130 may be disposed within guidewire lumen 164 such that scoring balloon catheter 102 may be advanced over guidewire 130 and through a patient's vasculature to a targeted stenotic region. Catheter shaft 104 may be made from any suitable material, such as, but not limited to polyamide (PA) and polyether block amide (PEBA).

Figure 3:
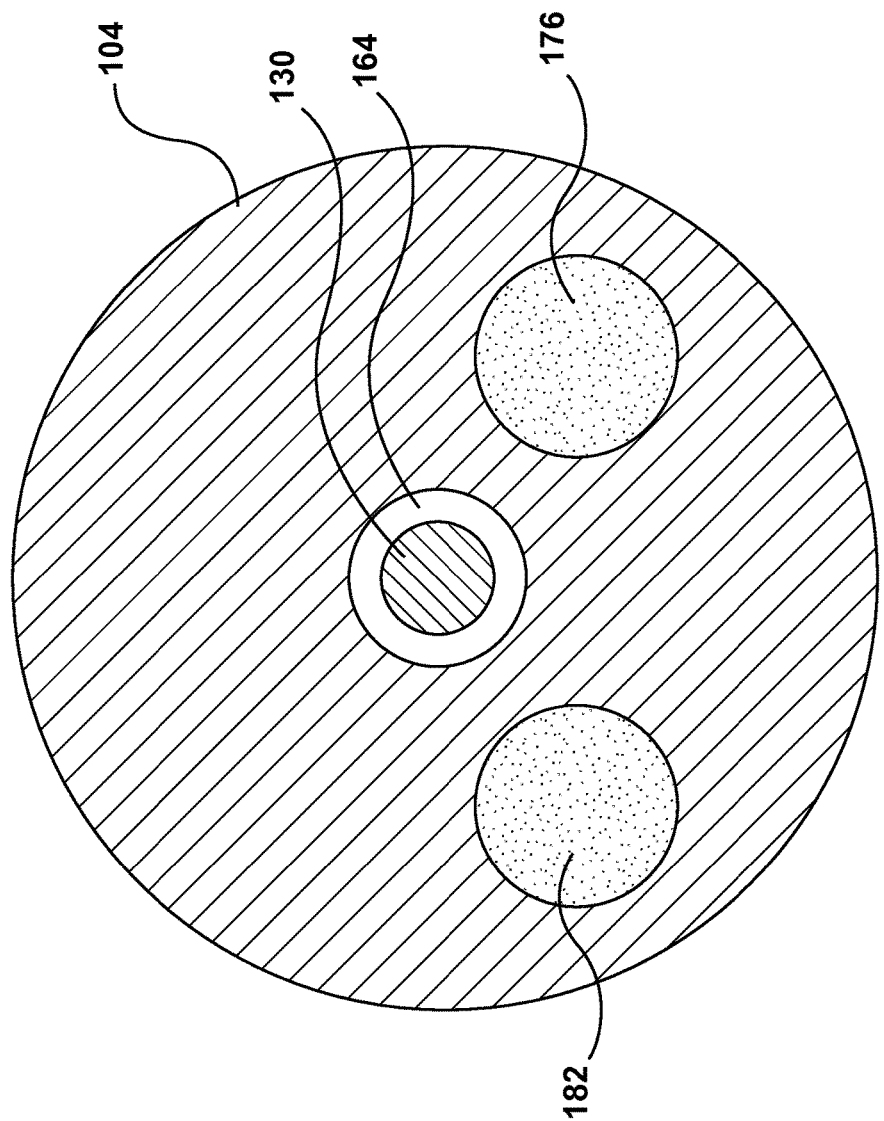
FIG. 3 is a cross sectional view of a catheter shaft of the scoring balloon catheter of FIG. 2.
Figure 4:
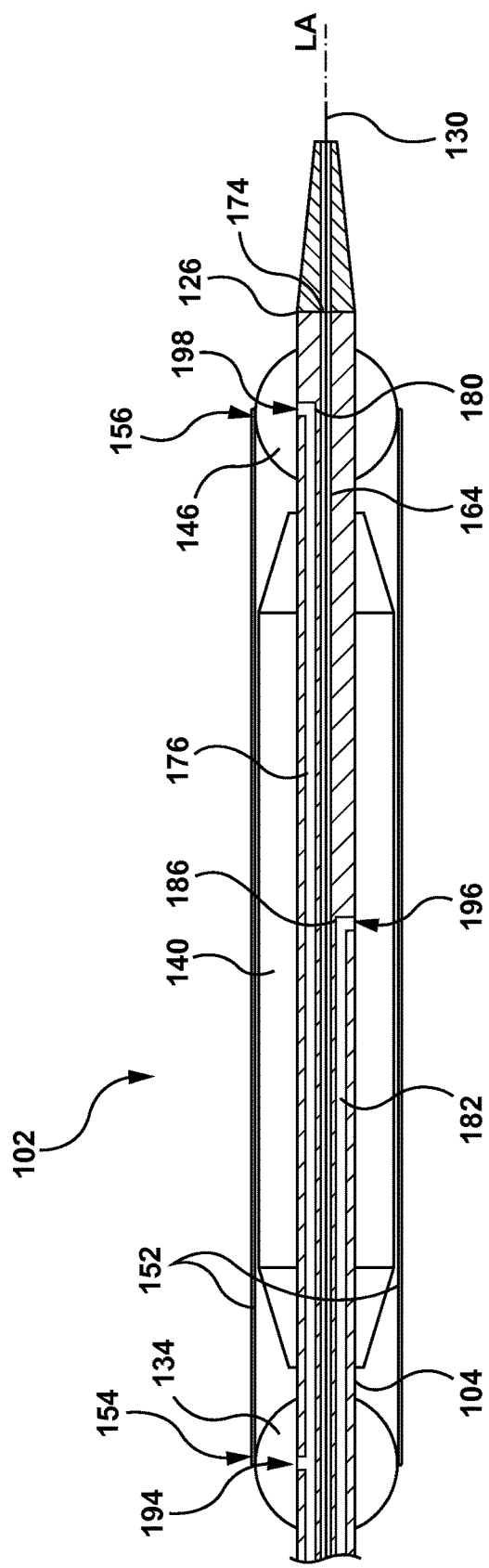
FIG. 4 is a cutaway side view of a distal portion the scoring balloon catheter of FIG. 2 with the proximal and distal control balloons and the scoring balloon inflated.
Figure 5:
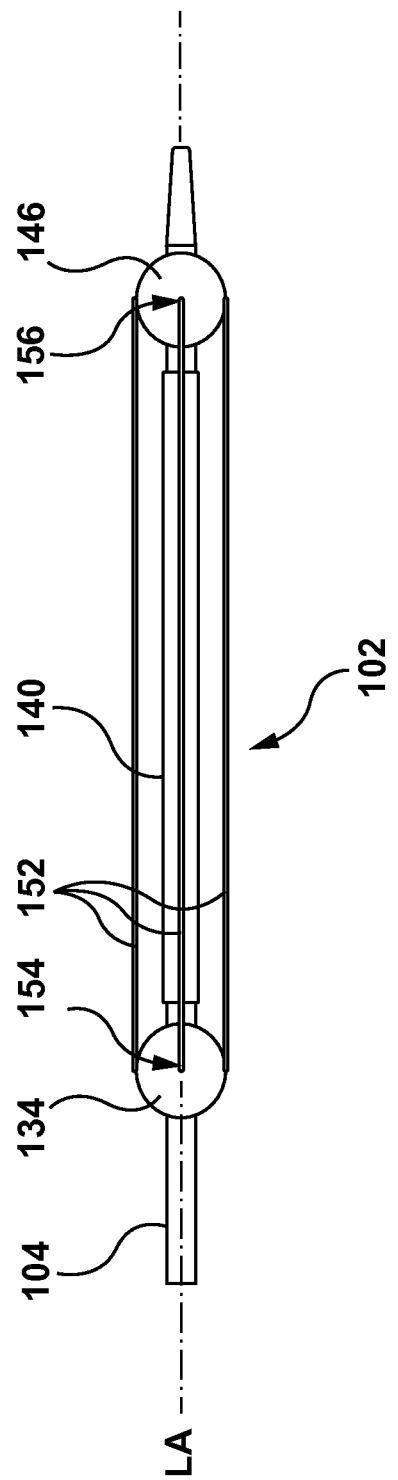
FIG. 5 is a side illustration of the distal portion of the scoring balloon catheter of FIG. 1 with the proximal and distal control balloons inflated and the scoring balloon not inflated.

Proximal control balloon 134, scoring balloon 140, and distal control balloon 146 are shown in an uninflated, or delivery configuration in FIG. 2, and in an inflated, or expanded configuration in FIG. 4. In the embodiment shown in FIGS. 2-4, scoring balloon catheter 102 has an over-the-wire (OTW), multi-lumen configuration with guidewire lumen 164 (FIG. 1) extending substantially the entire length of scoring balloon catheter 102, as previously described, for accommodating guidewire 130. Catheter shaft 104 includes a proximal end 106 that extends out of the patient and is coupled to hub 132, and a distal end 126 coupled to a distal tip 128. Proximal control balloon 134 has a proximal end 136 coupled to catheter shaft 104 and a distal end 138 coupled to catheter shaft 104. Scoring balloon 140 has a proximal end 142 coupled to catheter shaft 104 distal of distal end 138 of proximal control balloon 134, and a distal end 144 coupled to catheter shaft 104 distal of proximal end 142. Distal control balloon 146 has a proximal end 148 coupled catheter shaft 104 distal of distal end 144 of scoring balloon 140, and a distal end 150 coupled catheter shaft 104 distal of proximal end 148. Distal tip 128 is disposed distal of distal end 150 of distal control balloon 146.

A plurality of lumens are defined within catheter shaft 104, as shown in FIG. 3-4. Catheter shaft 104 defines guidewire lumen 164, as explained above, a first inflation lumen 176, and a second inflation lumen 178. In the embodiment shown, guidewire lumen 164 is co-axial with longitudinal axis LA. Guidewire lumen 164 has a proximal end (not shown) at proximal end 106 of catheter shaft 104, and a distal end (not shown) at distal end 126 of catheter shaft 104.

First inflation lumen 176 has a proximal end (not shown) at proximal end 106 of catheter shaft 104, and a distal end 180 in fluid communication with a distal control balloon inflation port 198, as shown in FIG. 4. Distal control balloon inflation port 198 is in fluid communication with an interior of distal control balloon 146. First inflation lumen 176 is also in fluid communication with a proximal control balloon inflation port 194 between the proximal end of first inflation lumen 176 and distal end 180 of first inflation lumen 176. Proximal control balloon inflation port 194 is in fluid communication with an interior of proximal control balloon 134.

Second inflation lumen 182 has a proximal end (not shown) at proximal end 106 of catheter shaft 104, and a distal end 186 in fluid communication with a scoring balloon inflation port 196. Scoring balloon inflation port 196 is in fluid communication with an interior of scoring balloon 140. Second inflation lumen 182, scoring balloon inflation port 196, and scoring balloon 140 are configured such that an interior of scoring balloon 140 is in fluid communication with the proximal end of second inflation lumen 182.

In the embodiment shown, first inflation lumen 176 and second inflation lumen 182 are configured such that proximal and distal control balloons 134, 146 inflate/uninflate in unison with each other, and scoring balloon 140 inflates/uninflates independent of proximal and distal control balloons 134/146. The proximal ends of first and second inflation lumens 176, 182 allow inflation fluid received through an inflation port (not shown) of hub 132 to be delivered to proximal and distal control balloon 134, 146, and scoring balloon 140, respectively. As would be understood by one of ordinary skill in the art of balloon catheter design, hub 132 provides a luer hub or other type of fitting that may be connected to a source of inflation fluid and may be of another construction or configuration without departing from the scope of the present invention.

Scoring balloon 140 is coupled to scoring balloon catheter 102 as previously described and shown in FIGS. 1-4. Scoring balloon 140 includes an uninflated, or delivery configuration in which scoring balloon 140 is not inflated (FIGS. 2, 5), and an inflated, or expanded configuration wherein scoring balloon 140 is inflated (FIG. 6) via inflation fluid delivered through second inflation lumen 182 to an interior of scoring balloon 140. Scoring balloon 140 may be a standard construction, non-compliant or semi-compliant balloon constructed of any suitable material, such as, but not limited to, polyethylene terephthalate (PET), nylon, PEBA, or polyurethane. Scoring balloon diameter ranges from 1 mm-30 mm and may be any length as required by the application.

Proximal control balloon 134 is positioned proximal of scoring balloon 140. Distal control balloon 146 is positioned distal of scoring balloon 140. Proximal control balloon 134 and distal control balloon 146 are coupled to scoring balloon catheter 102 as previously described. Proximal and distal control balloons 134/146 have an uninflated, or delivery configuration in which proximal and distal control balloons 134/146 are not inflated (FIG. 2), and an inflated, or expanded configuration in which proximal and distal control balloons 134/146 are inflated (FIGS. 5-6) via inflation fluid delivered through first inflation lumen 176 to an interior of proximal and distal control balloons 134/146. Proximal and distal control balloons 134/146 may be a standard construction compliant balloon constructed of any suitable material, such as, but not limited to, nylon, plastic rubber, and polyurethane. Control balloon diameter ranges from 1 mm-30 mm and may be any length as required by the application.

Figure 6:
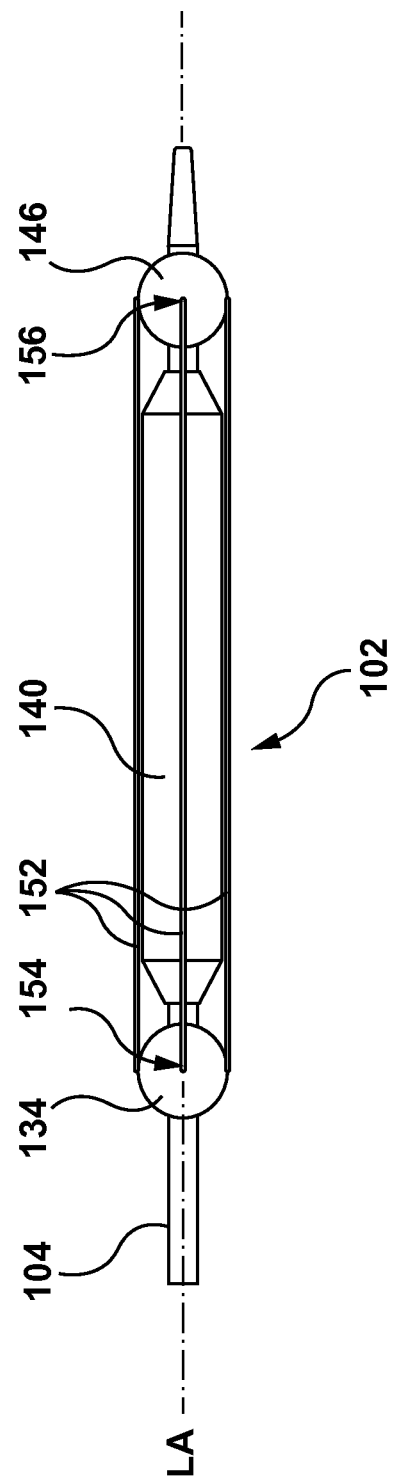
FIG. 6 is a side illustration of the distal portion of the scoring balloon catheter of FIG. 1 with the proximal and distal control balloons inflated and the scoring balloon inflated.

A plurality of scoring elements 152 are coupled to proximal and distal control balloons 134/146. A distal end 156 of each scoring element 152 is coupled to distal control balloon 146, and a proximal end 154 of each scoring element 152 is coupled to proximal control balloon 134, as shown in FIG. 6. While the embodiment shown in FIG. 6 shows four scoring elements 152, this is not meant to limit the design, and more or fewer scoring elements 152 may be used as required by the application. Scoring elements 152 have a first, relaxed configuration corresponding to the un-inflated configuration of proximal and distal control balloons 134/146. Scoring elements 152 have a second, taut configuration corresponding to the inflated configuration of proximal and distal control balloons 134/146. Scoring elements 152 have a third, expanded configuration corresponding to the inflated configuration of scoring balloon 140. Scoring elements 152 may be constructed of any suitable material, such as, but not limited to, nitinol and stainless steel wire. Scoring elements 152 may be of any shape suitable for the application including, but not limited to circular, rectangular, or square wire.

Figure 7:
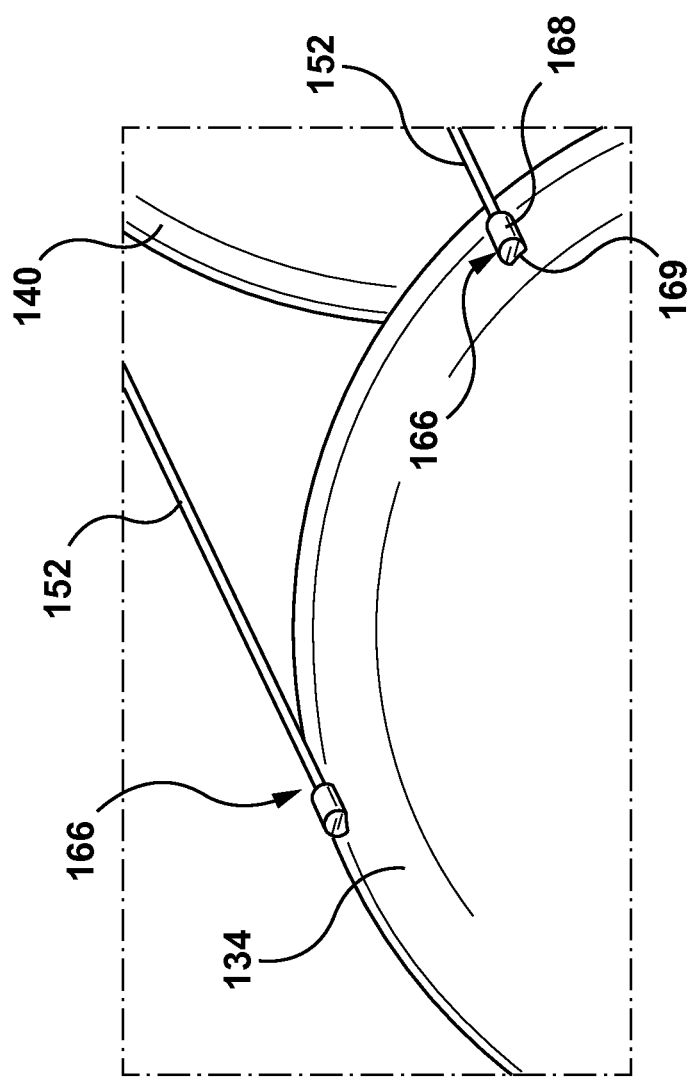
FIG. 7 is a close-up illustration of the proximal control balloon of the scoring balloon catheter of FIG. 1 illustrating the scoring element bonding point.

Scoring elements 152 are coupled to proximal and distal control balloons 134/146 at a scoring element bonding points 166, shown in greater detail in FIG. 7. Each scoring element 152 may be coupled to proximal and distal balloons 134/146 by any method, including, but not limited to glue and other polymer adhesives. The ends of each scoring element 152 may be overmolded with a polymeric material 168 to enhance bonding adhesion, as shown in FIG. 7. Further, to enhance the surface area in contact with proximal and distal balloons 134/146 at scoring element bonding point 166, the ends of scoring element 152 or polymeric material 168 may be partially flattened to increase surface contact area, as shown at 169 of FIG. 7. Although FIG. 7 shows scoring element bonding points 166 at proximal control balloon 134, they may be the same for coupling distal ends 156 of scoring elements 152 to distal control balloon 146.

Figure 8:
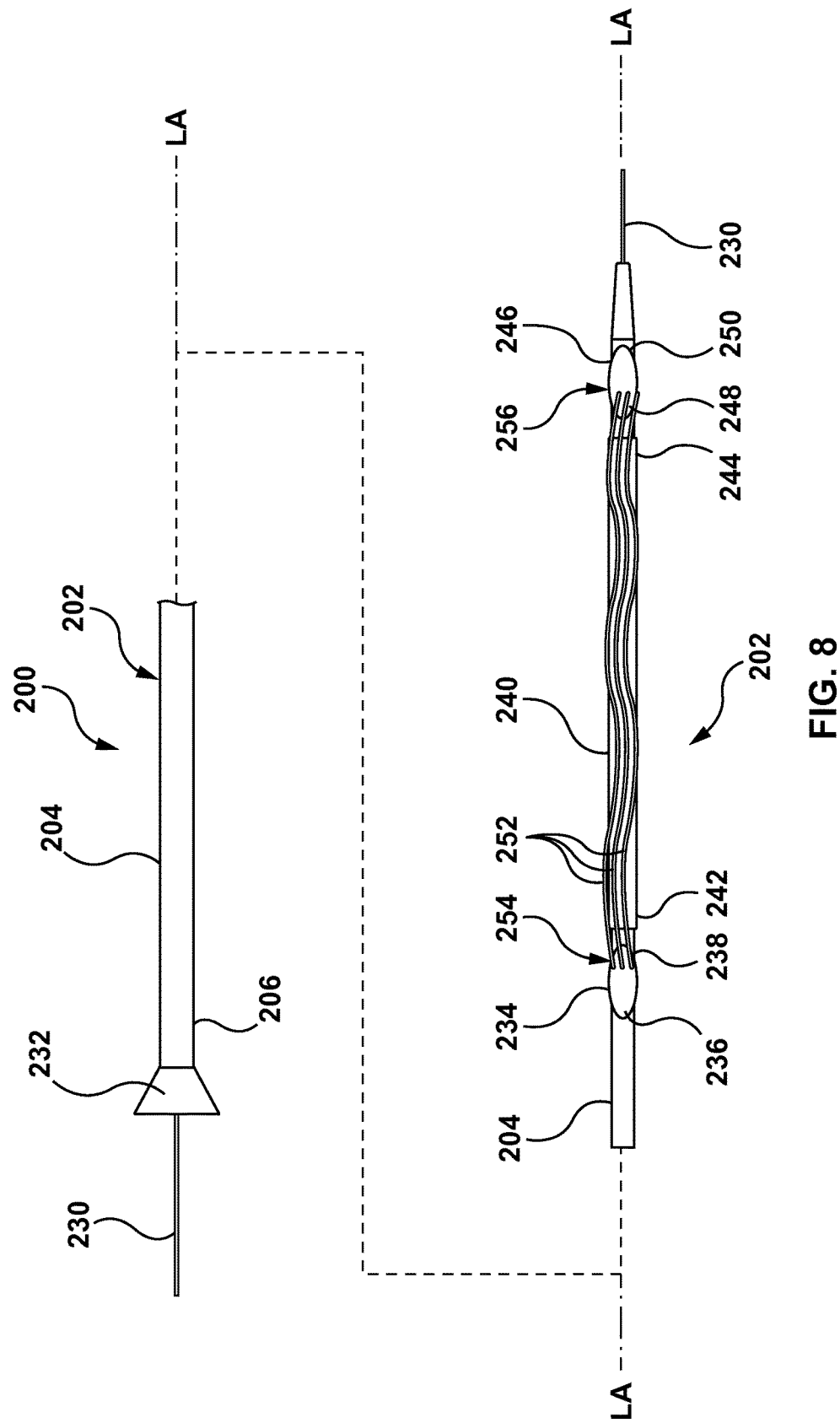
FIG. 8 is a side view of another embodiment of a scoring balloon catheter with the proximal and distal control balloons and the scoring balloon not inflated.
Figure 9:
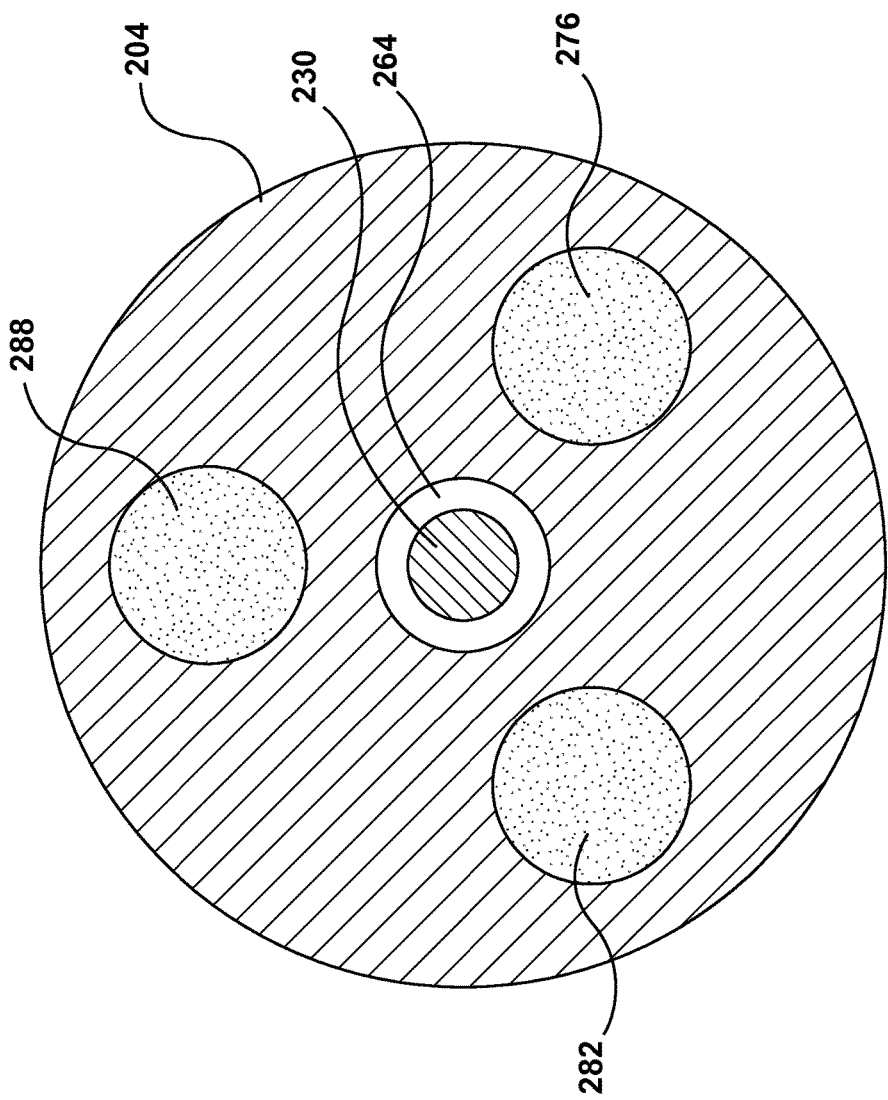
FIG. 9 is a cross sectional view of the scoring balloon catheter of FIG. 8.
Figure 10:
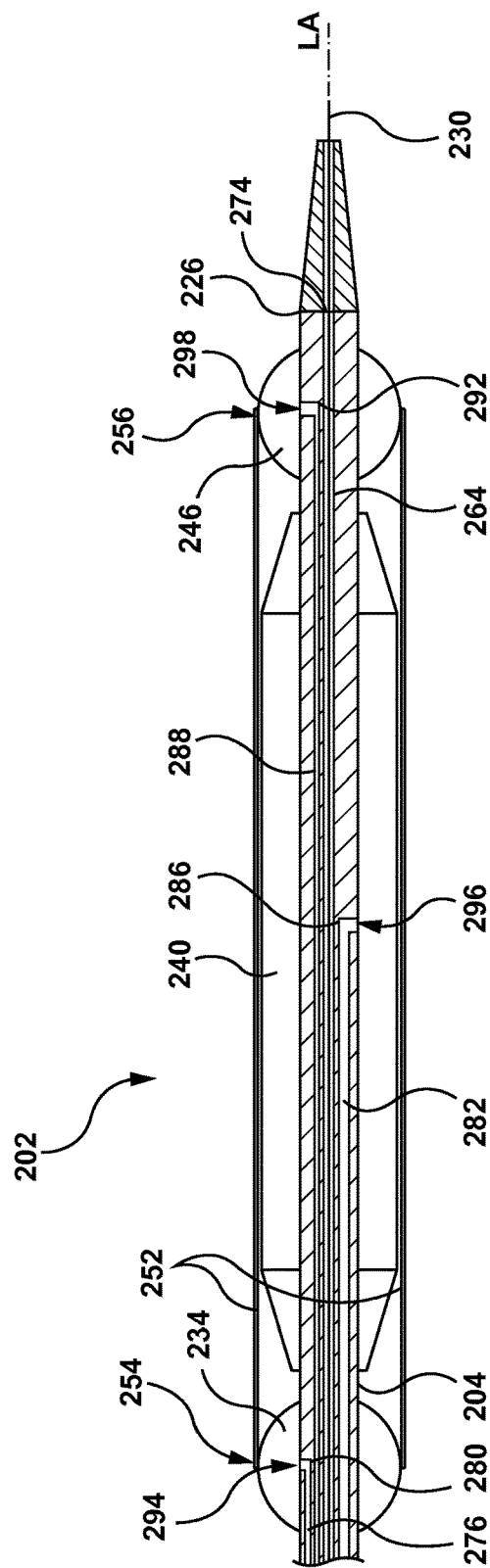
FIG. 10 is a cutaway side view of the scoring balloon catheter of FIG. 8 with the proximal and distal control balloons and the scoring balloon inflated.

FIGS. 8-10 show another embodiment of a catheter system 200 including scoring balloon catheter 202. In FIGS. 8-10, similar elements to the embodiment of FIGS. 1-7 use similar reference numerals except for the first digit thereof. The elements of the embodiment of FIGS. 8-10 which are not specifically identified as being different from the embodiment of FIGS. 1-7 may be the same as the embodiment of FIGS. 1-7 and the description thereof is incorporated into the description of FIGS. 8-10.

Scoring balloon catheter 202 of FIGS. 8-10 is a multi-lumen configuration with separate inflation lumens for a proximal control balloon 234 and a distal control balloon 246. Proximal control balloon 234, a scoring balloon 240, and distal control balloon 246 are shown in an uninflated, or delivery configuration in FIG. 10. In the embodiment shown in FIGS. 8-10, scoring balloon catheter 202 has an over-the-wire (OTW), multi-lumen configuration with a guidewire lumen 264 extending substantially the entire length of scoring balloon catheter 202, as previously described, for accommodating a guidewire 230, therein. Scoring balloon catheter 202 includes a catheter shaft 204, having a proximal end 206 that extends out of the patient and is coupled to a hub 232, and a distal end 226 coupled to a distal tip 228.

Proximal control balloon 234 includes a proximal end 236 coupled catheter shaft 204 and a distal end 238 coupled to catheter shaft 204 distal to proximal end 236. Scoring balloon 240 includes a proximal end 242 catheter shaft section 204 distal of distal end 238 of proximal balloon 234, and a distal end 244 coupled to catheter shaft 204 distal of proximal end 242. Distal control balloon 246 includes a proximal end 248 coupled to catheter shaft 204 distal of distal end 244 of scoring balloon 240, and a distal end 250 coupled to catheter shaft 204 distal of proximal end 248.

A plurality of lumens are defined within catheter shaft 204, as shown in FIGS. 9-10. Catheter shaft 204 defines guidewire lumen 264, a first inflation lumen 276, a second inflation lumen 288, and a third inflation lumen 282. Guidewire lumen 264 accommodates guidewire 230 as described above and extends along longitudinal axis LA of catheter shaft 204. Guidewire lumen 264 has a proximal end (not shown) at proximal end 206 of catheter shaft 204, and a distal end 274 at distal end 226 of catheter shaft 204.

First inflation lumen 276 has a proximal end (not shown) at proximal end 206 of catheter shaft 204, and a distal end 280 in fluid communication with a proximal control balloon inflation port 294, as shown in FIG. 10. Proximal control balloon inflation port 294 is in fluid communication with an interior of proximal control balloon 234.

Second inflation lumen 288 has a proximal end (not shown) at proximal end 206 of catheter shaft 204, and a distal end 292 in fluid communication with a distal control balloon inflation port 298, as shown in FIG. 10. Distal control balloon inflation port 298 is in fluid communication with an interior of distal control balloon 246.

Third inflation lumen 282 has a proximal end (not shown) at proximal end 206 of catheter shaft 204, and a distal end 286 in fluid communication with a scoring balloon inflation port 296. Scoring balloon inflation port 296 is in fluid communication with an interior of scoring control balloon 240.

In the embodiment of FIGS. 8-10, first inflation lumen 276, second inflation lumen 288, and third inflation lumen 282 are configured such that proximal control balloon 234, scoring balloon 240, and distal control balloon 246, respectively, all inflate/uninflate independent of each other, if desired. They may be inflated together if each inflation lumen is filled with inflation fluid at the same time. The proximal ends of first, second, and inflation lumens 176, 182, 188 allow inflation fluid received through an inflation port (not shown) of hub 232 to be delivered to proximal balloon 234, scoring balloon 240, and distal control balloon 246, respectively. As would be understood by one of ordinary skill in the art of balloon catheter design, hub 232 provides a luer hub or other type of fitting that may be connected to a source of inflation fluid and may be of another construction or configuration without departing from the scope of the present invention.

As explained above, scoring balloon 240 is coupled to scoring balloon catheter 202. Scoring balloon 240 includes an uninflated, or delivery configuration in which scoring balloon 240 is not inflated, and an inflated, or expanded configuration in which scoring balloon 240 is inflated via inflation fluid delivered through third inflation lumen 282 to an interior of scoring balloon 240. Scoring balloon 240 may be a standard construction, non-compliant or semi-compliant balloon constructed of any suitable material, such as, but not limited to, polyethylene terephthalate (PET), nylon, PEBA, or polyurethane. Scoring balloon diameter ranges from 1 mm-30 mm and may be any length as required by the application.

Proximal control balloon 234 is positioned proximal of scoring balloon 240. Distal control balloon 246 is positioned distal of scoring balloon 240. Proximal control balloon 234 and distal control balloon 246 are coupled to catheter shaft 204 as previously described. Proximal and distal control balloons 234/246 have an uninflated, or delivery configuration in which proximal and distal control balloons 234/246 are not inflated, and an inflated, or expanded configuration in which proximal and distal control balloons 234/246 are inflated via inflation fluid delivered through first and second inflation lumens 276, 288 to an interior of proximal and distal control balloons 234/246, respectively. Proximal and distal control balloons 234/246 may be a standard construction compliant balloon constructed of any suitable material, such as, but not limited to, nylon, plastic rubber, and polyurethane. Control balloon diameter ranges from 1 mm-30 mm and may be any length as required by the application.

A plurality of scoring elements 252 are coupled to proximal and distal control balloons 234/246. A distal end 256 of scoring element 252 is coupled to distal control balloon 246, and a proximal end 254 of scoring element 252 is coupled to proximal control balloon 234. Each scoring element 252 may be coupled to proximal and distal control balloons 234/246 as described above with respect to FIG. 7. While the embodiment shown in FIGS. 8-10 includes four scoring elements disposed equally around the circumference of catheter shaft 204 (two shown in cross-section), this is not meant to limit the design, and more or fewer scoring elements 252 may be included as required by the application. Scoring elements 252 include a first, relaxed configuration corresponding to the uninflated configuration of proximal and distal control balloons 234/246. Scoring elements 252 include a second, taut configuration corresponding to the inflated configuration of proximal and distal control balloons 234/246. Scoring elements 252 include a third, expanded configuration corresponding to the inflated configuration of scoring balloon 240. Scoring elements 252 may be constructed of any suitable material, such as, but not limited to, nitinol and stainless steel wire. Scoring elements 252 may be of any shape suitable for the application including, but not limited to circular, rectangular, or square wire.

Figure 11:
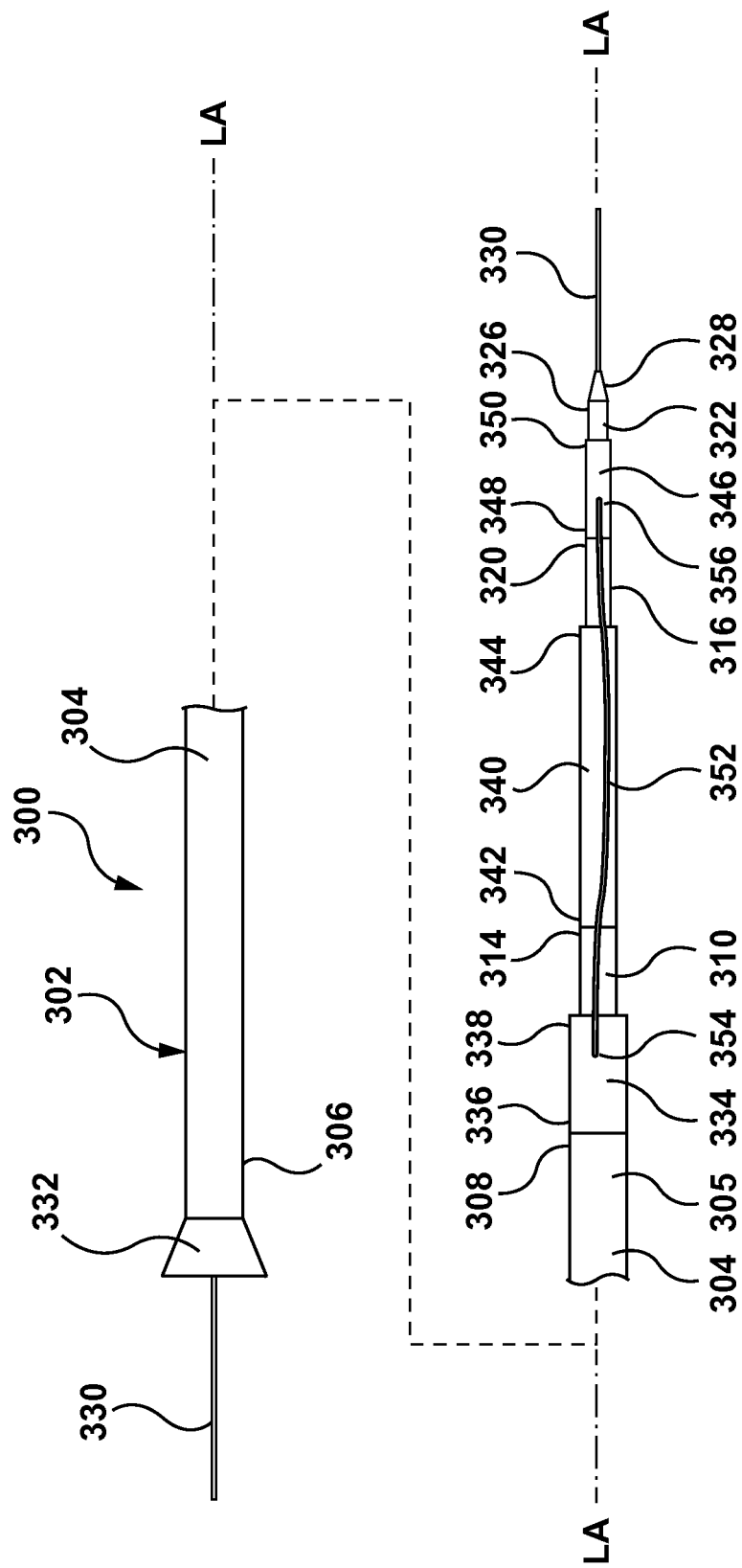
FIG. 11 is a side view of another embodiment of a scoring balloon catheter with the proximal and distal control balloons and the scoring balloon not inflated.
Figure 12:
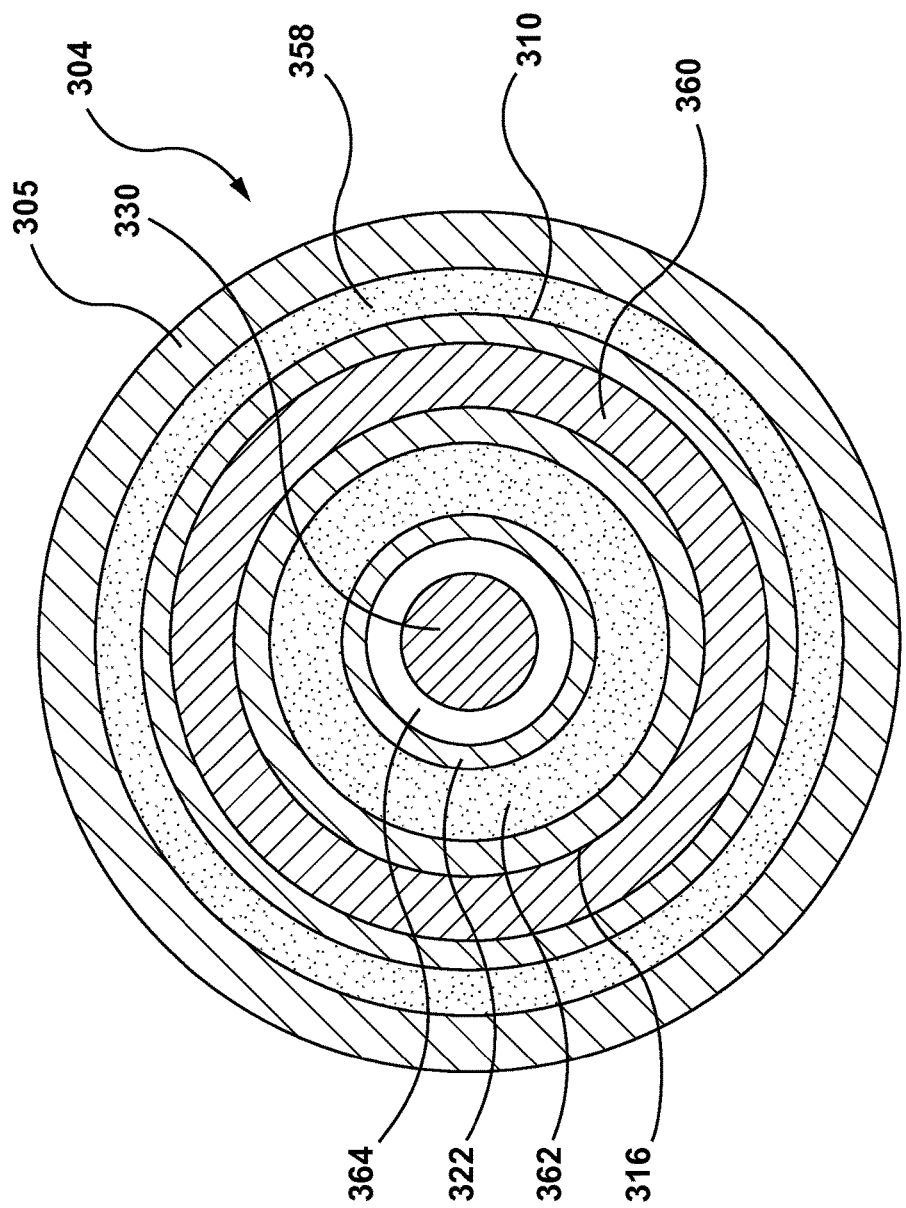
FIG. 12 is a cross sectional view the scoring balloon catheter of FIG. 11.

FIGS. 11-12 show another embodiment of a catheter system 300 including a scoring balloon catheter 302, a hub 332, and a guidewire 330. In FIGS. 11-12, similar elements to the embodiment of FIGS. 1-7 and FIGS. 8-10 use similar reference numerals except for the first digit thereof. The elements of the embodiment of FIGS. 11-12 which are not specifically identified as being different from the embodiment of FIG. 1-7 or 8-10 may be the same as the embodiment of FIG. 1-7 or 8-10 and the description thereof is incorporated into the description of FIGS. 11-12.

Scoring balloon catheter 302 includes a catheter shaft 304, a proximal control balloon 334, a scoring balloon 340, a distal control balloon 346, and a plurality of scoring elements 352. In this embodiment, catheter shaft 304 may be of a coaxial catheter construction including a plurality of shafts disposed co-axially around each other, as described in more detail below. Catheter shaft 304 includes a longitudinal axis LA. Catheter shaft 304 includes a proximal end 306 that extends out of the patient and is coupled to hub 332.

In the coaxial catheter construction of the embodiment of FIGS. 11-12, catheter shaft 304 includes a guidewire shaft 322 defining a guidewire lumen 364, an inner control shaft 316 disposed around guidewire shaft 322, an inner scoring shaft 310 disposed around inner control shaft, and an outer shaft 305 disposed around inner scoring shaft 310. A first inflation lumen 358 is defined between an inner surface of outer shaft 305 and an outer surface of inner scoring shaft 310, as shown in FIG. 14. A second inflation lumen 360 is defined between an inner surface of inner scoring shaft 310 and an outer surface of inner control shaft 316. A third inflation lumen 362 is defined between an inner surface of inner control shaft 316 and an outer surface of guidewire shaft 322.

Proximal control balloon 334, scoring balloon 340, and distal control balloon 346 are shown in an uninflated, or delivery configuration in FIG. 11. Proximal control balloon 334 includes a proximal end 336 coupled to a distal end 308 of outer shaft 305, and a distal end 338 coupled to inner scoring shaft 310 proximal of a distal end 314 of inner scoring shaft 310. Scoring balloon 340 includes a proximal end 342 coupled to distal end 314 of inner scoring shaft 310, and a distal end 344 coupled to inner control shaft 316 proximal of a distal end 320 of inner control shaft 316. Distal control balloon 346 includes a proximal end 348 coupled to distal end 320 of inner control shaft 316, and a distal end 350 coupled to guidewire shaft 322 proximal of a distal end 326 of guidewire shaft 322. Guidewire shaft 322 includes a proximal end (not shown) coupled to hub 332, and a distal end 326 terminating distally of distal control balloon 346, and coupled to a distal tip 328. Outer shaft 305, inner scoring shaft 310, and inner control shaft 316 include proximal ends (not shown) coupled to hub 332.

As can be seen by the manner in which proximal control balloon 334, scoring balloon 340, and distal control balloon 346 are coupled to outer shaft 305, inner scoring shaft 310, inner control shaft 316, and guidewire shaft 322, first inflation lumen 358 is in fluid communication with an interior of proximal control balloon 346, second inflation lumen 360 is in fluid communication with an interior of scoring balloon 340, and third inflation lumen 362 is in fluid communication with an interior of distal control balloon 346, respectively. The proximal ends of first, second, and third inflation lumens 358, 360, 362 allow inflation fluid received through an inflation port (not shown) of hub 332 to be delivered to proximal control balloon 334, scoring balloon 340, and distal control balloon 346, respectively. As would be understood by one of ordinary skill in the art of balloon catheter design, hub 332 provides a luer hub or other type of fitting that may be connected to a source of inflation fluid and may be of another construction or configuration without departing from the scope of the present invention. With a separate inflation lumen in communication with a respective one of the balloons, proximal control balloon 334, scoring balloon 340, and distal control balloon 346 may be inflated independent of each other. Alternatively, the source of inflation fluid may provide inflation fluid to two or more of the inflation lumens simultaneously to inflate the respective balloons simultaneously.

Scoring balloon 340 is coupled to scoring balloon catheter 302 as previously described and shown in FIGS. 11-12. Scoring balloon 340 has an uninflated, or delivery configuration in which scoring balloon 340 is not inflated, and an inflated, or expanded configuration in which scoring balloon 340 is inflated. Scoring balloon 340 may be a standard construction, non-compliant or semi-compliant balloon constructed of any suitable material, such as, but not limited to, polyethylene terephthalate (PET), nylon, PEBA, or polyurethane. Scoring balloon diameter ranges from 1 mm-30 mm and may be any length as required by the application.

Proximal control balloon 334 is positioned proximal of scoring balloon 340. Distal control balloon 346 is positioned distal of scoring balloon 340. Proximal and distal control balloons 334/346 are coupled to scoring balloon catheter 302 as previously described. Proximal and distal control balloons 334/346 have an uninflated, or delivery configuration in which proximal and distal control balloons 334/346 are not inflated, and an inflated or expanded configuration in which proximal and distal control balloons 334/346 are inflated. Proximal and distal control balloons 334/346 may be a standard construction compliant balloon constructed of any suitable material, such as, but not limited to, nylon, plastic rubber, and polyurethane. Control balloon diameter ranges from 1 mm-30 mm and may be any length as required by the application.

A plurality of scoring elements 352 are coupled to proximal and distal control balloons 334/346. A distal end 356 of each scoring element 352 is coupled to distal control balloon 346, and a proximal end 354 of each scoring element 352 is coupled to proximal control balloon 334. Each scoring element 352 may be coupled to proximal and distal control balloons 334/346 as described above with respect to FIG. 7. While the embodiment shown in FIG. 11 includes four scoring elements 352 disposed equally around the circumference of catheter shaft 304 (two shown in cross-section), this is not meant to limit the design, and more or fewer scoring elements 352 may be included as required by the application. Scoring elements 352 have a first relaxed configuration corresponding to the uninflated configuration of proximal and distal control balloons 334/346. Scoring elements 352 have a second taut configuration corresponding to the inflated configuration of proximal and distal control balloons 334/346. Scoring element 352 has a third expanded configuration corresponding to the inflated configuration of scoring balloon 340. Scoring elements 352 may be constructed of any suitable material, such as, but not limited to, nitinol wire. Scoring elements 352 may be of any shape suitable for the application including, but not limited to circular, rectangular, or square wire.

While the embodiments disclosed herein describe over-the-wire scoring balloon catheters, those skilled in the art would recognize that other types of balloon catheters, such as rapid exchange catheters, may also be used.

Figure 13A:
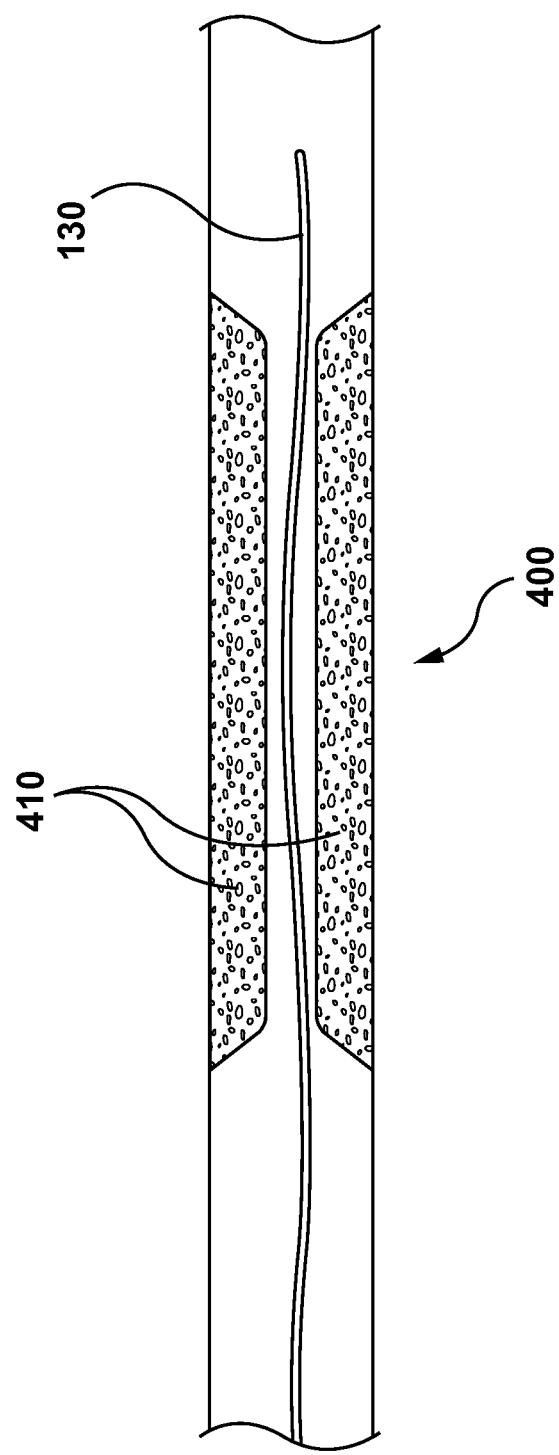
FIGS. 13A-13F are illustrations of a method for scoring a lesion within a patient's vasculature using the scoring balloon catheter of the present disclosure.
Figure 13B:
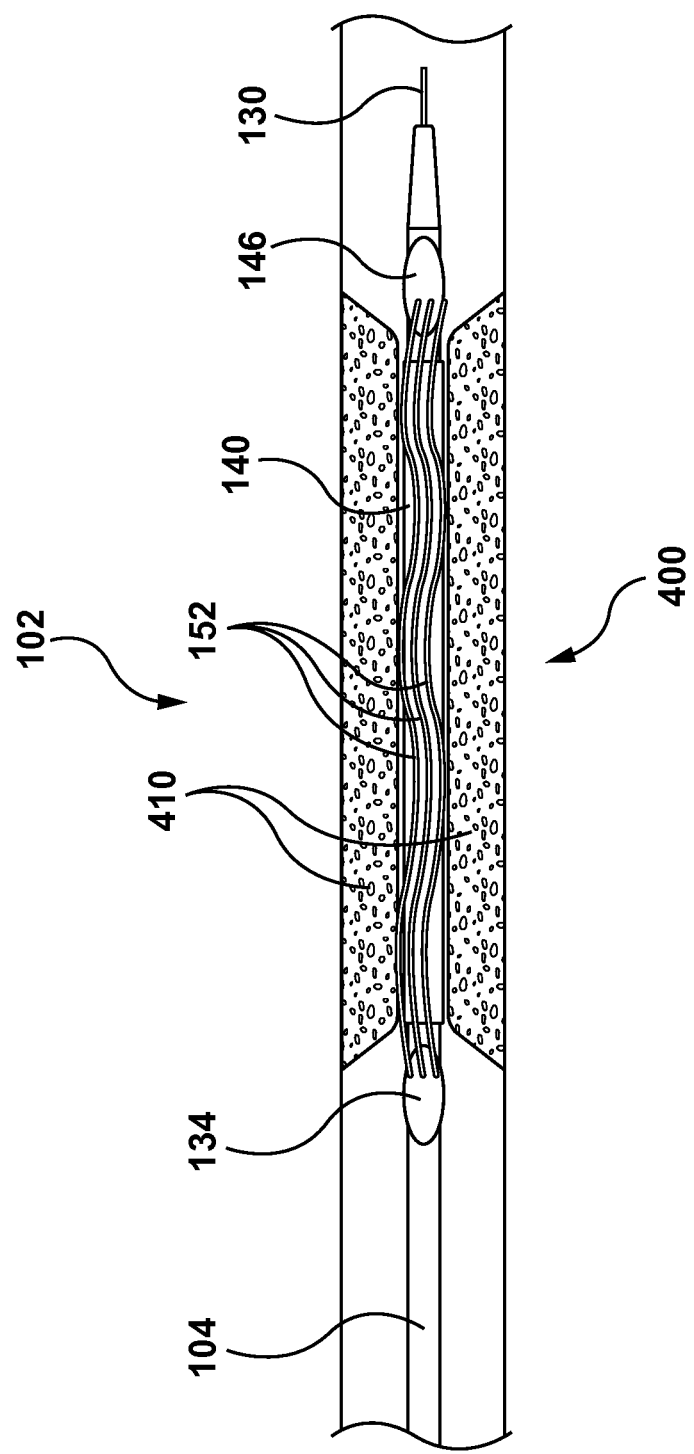

In some embodiments, catheter system 100, 200, 300 can be used in conjunction with a method to treat a stenotic lesion 410 in a vessel 400, as shown in FIGS. 13A-13F. While FIGS. 13A-13F describe the method using catheter system 100, catheter system 200 or catheter system 300 may be used instead in the method. Guidewire 130 is introduced and advanced through a patient's vasculature, beyond stenotic lesion 410, using standard percutaneous transluminal catheter (PCTA) procedures, as shown in FIG. 13A. Once guidewire 130 is in place, scoring balloon catheter 102 is advanced over guidewire 130 until positioned at a desired location within stenotic lesion 410, as shown in FIG. 13B. Scoring balloon catheter 102 is advanced through patient's vasculature 410, with scoring balloon 140 and proximal and distal control balloons 134/146 in their uninflated configuration, and scoring elements 152 in their first relaxed configuration. Positioning may be accomplished by any suitable means, such as, but not limited to, radiopaque markers and ultrasound.

Figure 13C:
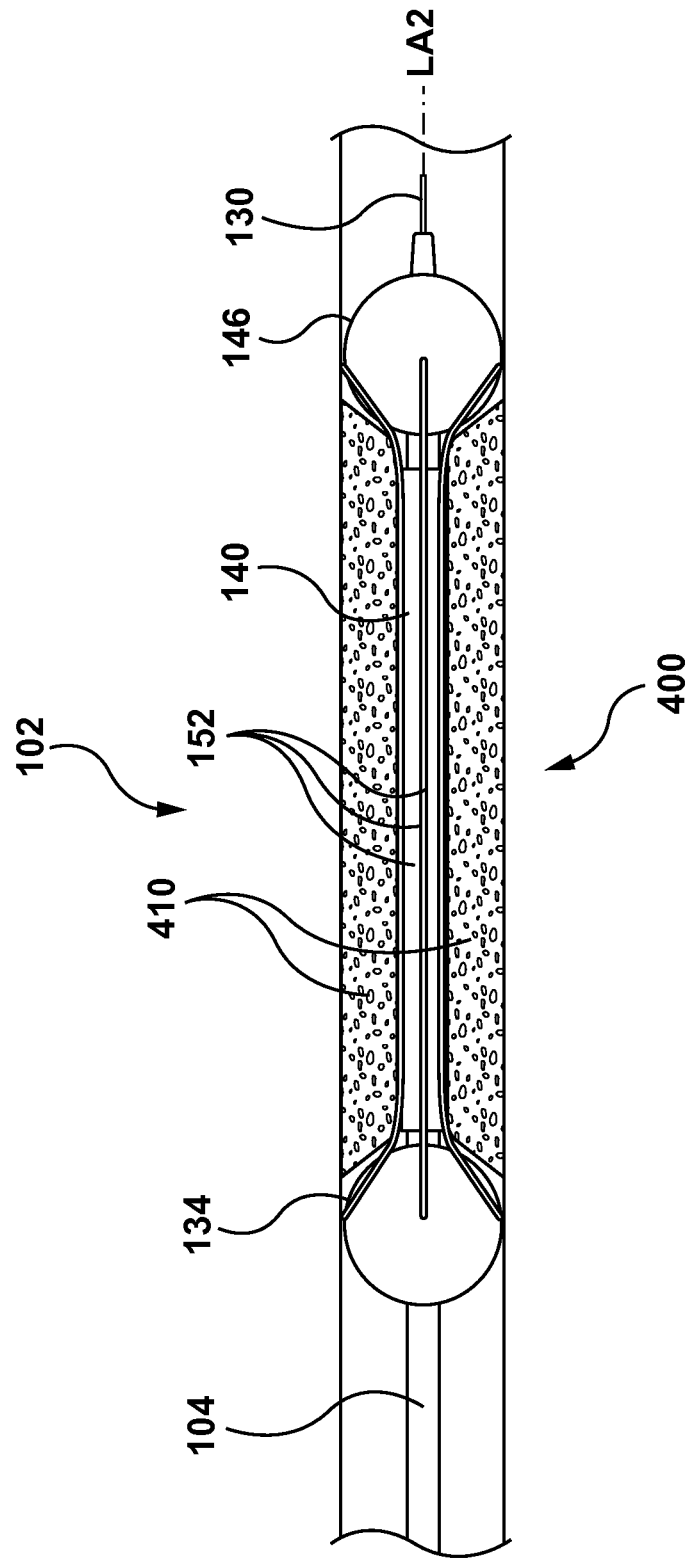

Once positioned within stenotic lesion 410, inflation fluid is pumped into proximal control balloon 134 and distal control balloon 146 such that proximal and distal control balloons 134/146 are inflated to their inflated configuration, as shown in FIG. 13C. Inflation of proximal and distal control balloons 134/146 radially expands proximal and distal control balloons 134/146, bringing their surface into contact with the inner surface of patient's vasculature 400. The contact of the proximal and distal control balloons 134/146 with the inner surface of patient's vessel 400 effectively stabilizes and maintains the desired position of scoring balloon catheter 102 during the remainder of the procedure. Additionally, as proximal and distal balloons 134/146 expand to their inflated configuration, scoring elements 152 are stretched from their first relaxed configuration to their second taut configuration. In their second taut configuration, the scoring elements 152 tend to align parallel to the longitudinal axis LA2 of the vessel 400. However, depending on the size of the stenotic lesion 410, scoring elements 152 may come into contact with the stenotic lesion 410, as shown in FIG. 13C, thus preventing scoring elements 152 from becoming fully parallel to the longitudinal axis LA2.

Figure 13D:
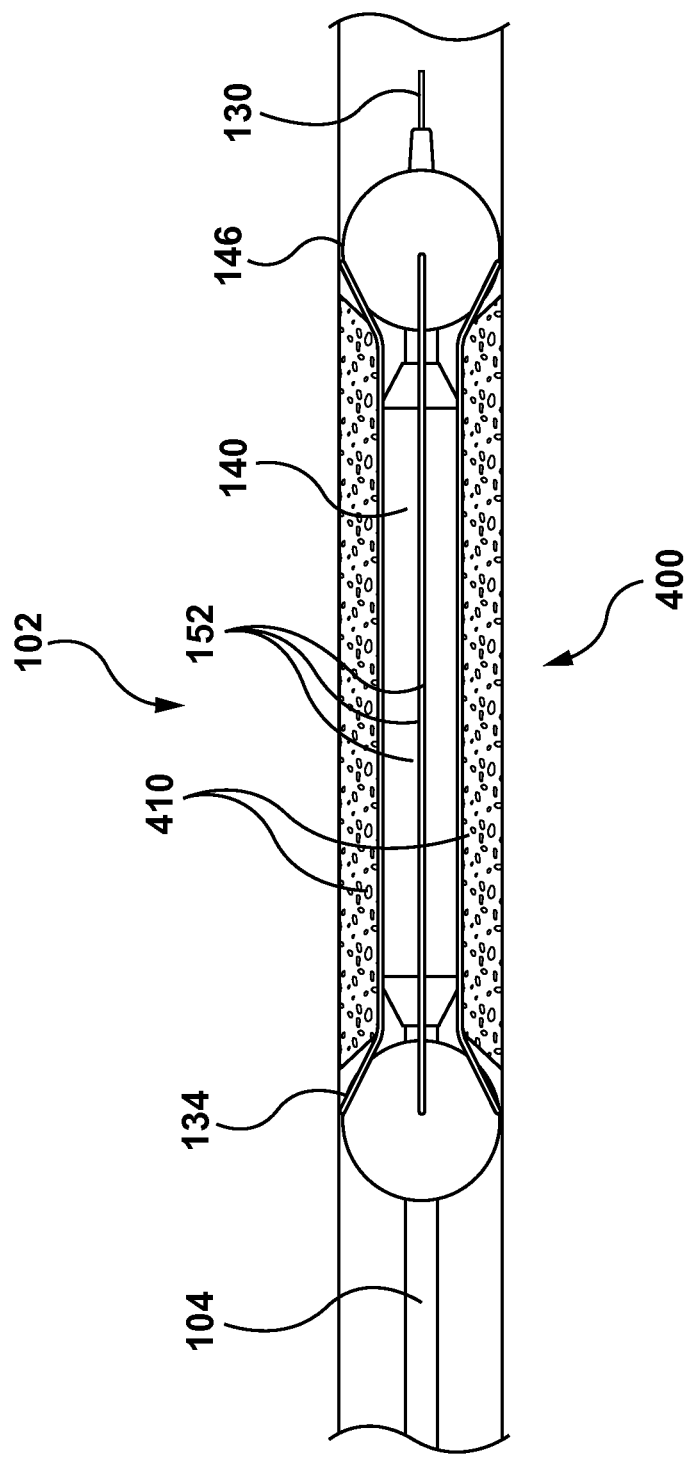

After proximal and distal control balloons 134/146 are expanded, inflation fluid is pumped into scoring balloon 140, and scoring balloon 140 begins to inflate, as shown in FIG. 13D. As scoring balloon 140 expands radially outward, it engages scoring elements 152. As more inflation fluid is pumped into scoring balloon 140, scoring balloon 140 continues to expand to its inflated configuration, forcing scoring elements 152 radially outward to their third expanded configuration. As scoring elements 152 are forced outward to their third expanded configuration by the radial expansion of scoring balloon 140, scoring elements 152 incise stenotic lesion 410. In the embodiment shown, the incisions are parallel with longitudinal axis LA2 of the treatment vessel 400. The combination of proximal and distal control balloons 134/146, scoring elements 152, and scoring balloon 140, work together to provide predictable dilation and vessel patency.

Figure 13E:
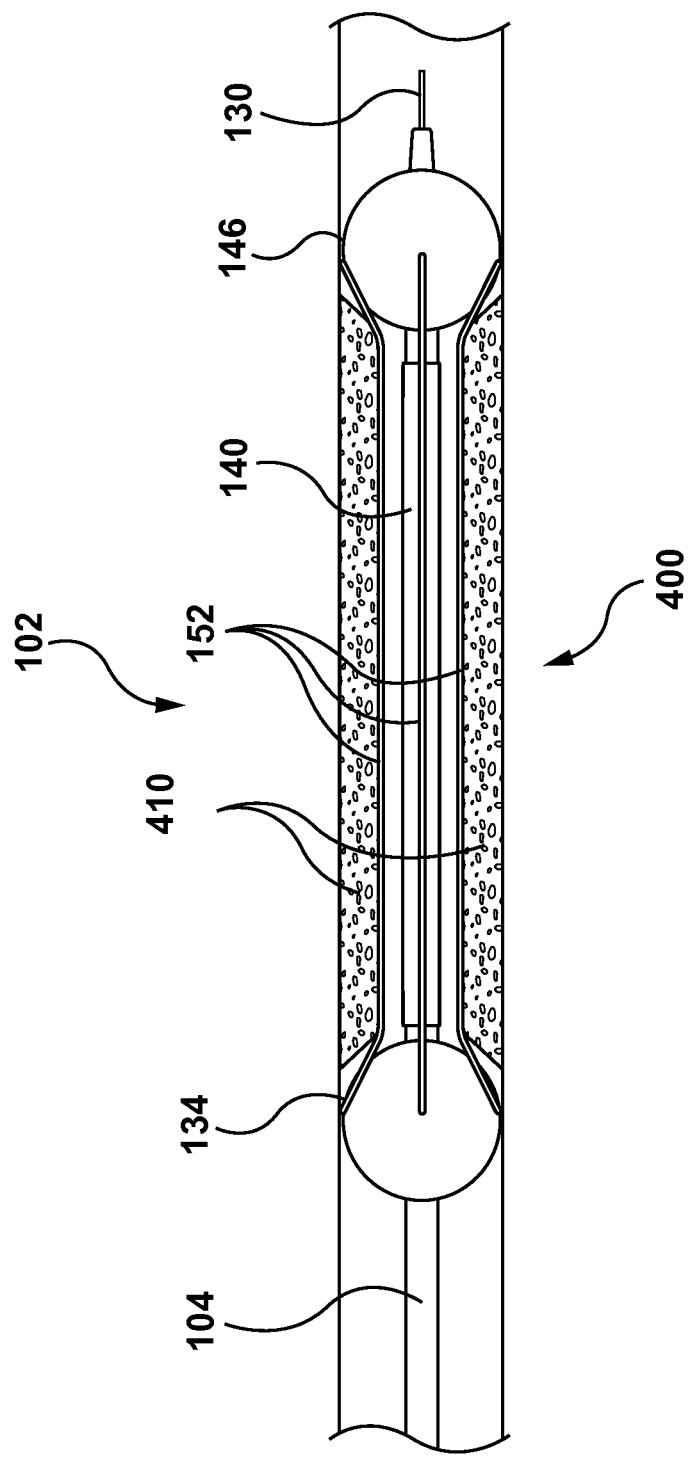

Once vessel patency has been achieved, the inflation fluid is drained from scoring balloon 140, such that scoring balloon 140 transitions from its inflated configuration to its uninflated configuration. As scoring balloon 140 radially contracts to its uninflated configuration, scoring elements 152 return to their second taut configuration, as shown in FIG. 13E.

Figure 13F:
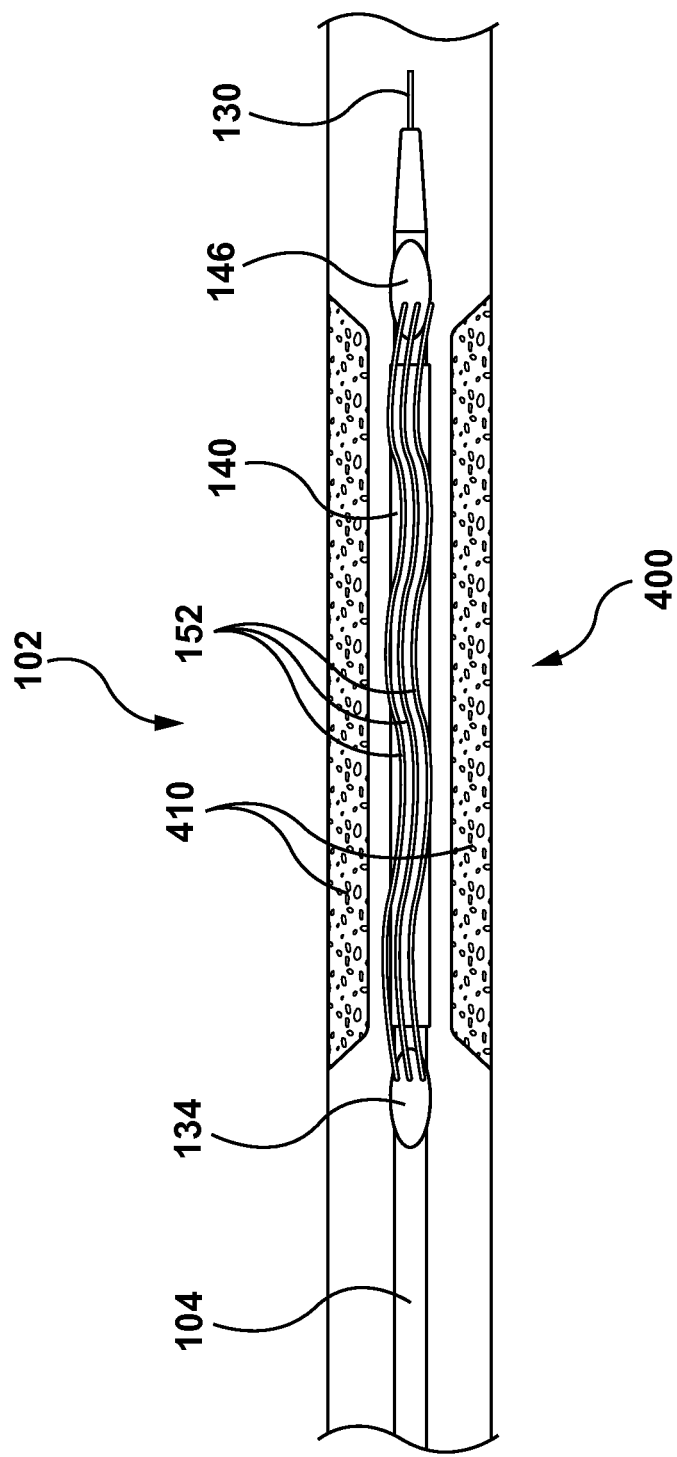

Next, inflation fluid is drained from proximal and distal control balloons 134/146, such that proximal and distal control balloon 134/146 transition from their inflated configuration to their uninflated configuration. As proximal and distal control balloons 134/146 contract to their uninflated configuration, scoring elements 152 return to their first relaxed configuration, as shown in FIG. 13F. Scoring balloon catheter 102 may now be retracted through patient's vasculature 410 using established procedures. Although deflation of the balloons has been explained sequentially, all the balloons may be deflated simultaneously.

Additional embodiments of the balloon catheter described herein may use the method described above. Independently inflated/uninflated control balloons may be inflated/uninflated either simultaneously, or in steps immediately following each other. While only some embodiments have been described herein, it should be understood that it has been presented by way of illustration and example only, and not limitation. Various changes in form and detail can be made therein without departing from the spirit and scope of the invention, and each feature of each embodiment discussed herein, and of each reference cited herein, can be used in combination with the features of any other embodiment.

What is claimed is:

1. A scoring balloon catheter for treating a site within a body lumen, the balloon catheter comprising:
   a scoring balloon;
   a distal control balloon distal of the scoring balloon;
   a proximal control balloon proximal of the scoring balloon;
   a scoring element coupled at a proximal end thereof to the proximal control balloon and at a distal end thereof to the distal control balloon, wherein with the proximal and distal control balloons each in an inflated configuration and the scoring balloon in an uninflated configuration, the scoring element is taut between the first and second control balloons and not in contact with the scoring balloon, wherein the scoring balloon is configured to expand to contact the scoring element, and wherein the scoring balloon is configured to be expanded separately from the proximal control balloon and the distal control balloon.

2. The scoring balloon catheter of claim 1, wherein the scoring element is parallel to a longitudinal axis of the balloon catheter with the proximal and distal control balloons in the inflated configuration.

3. The scoring balloon catheter of claim 1, wherein the scoring balloon is semi-compliant.

4. The scoring balloon catheter of claim 1, wherein the scoring balloon is non-compliant.

5. The scoring balloon catheter of claim 1, wherein the proximal and distal control balloons are compliant.

6. The scoring balloon catheter of claim 1, further comprising:
a catheter shaft, wherein the proximal control balloon, the scoring balloon, and the distal control balloon are coupled to the shaft; and
a first inflation lumen extending from a proximal end of the shaft and in fluid communication with an interior of each of the proximal and distal control balloons.

7. The scoring balloon catheter of claim 6, further comprising: a second inflation lumen extending from the proximal end of the catheter shaft and in fluid communication with an interior of the scoring balloon.

8. The scoring balloon catheter of claim 1, further comprising:
a catheter shaft, wherein the proximal control balloon, scoring balloon, and distal control balloon are coupled to the catheter shaft;
a first inflation lumen extending from the proximal end of the catheter shaft and in fluid communication with the proximal control balloon; and
a second inflation lumen extending from the proximal end of the catheter shaft and in fluid communication with the distal control balloon.

9. The scoring balloon catheter of claim 8, further comprising a third inflation lumen extending from the proximal end of the catheter shaft and in fluid communication with the scoring balloon.

10. The scoring balloon catheter of claim 1, wherein the scoring element comprises a plurality of scoring elements.

11. The scoring balloon catheter of claim 1, wherein the scoring element comprises a wire.

12. The scoring balloon catheter of claim 1, wherein with the proximal and distal control balloons in an uninflated configuration, the scoring element is relaxed.

13. The scoring balloon catheter of claim 1, wherein the scoring balloon includes an inflated configuration such that the scoring balloon comes into contact with the scoring element and the scoring element is forced radially outward.

14. A method for scoring a lesion within a patient's vasculature, the method comprising the steps of:
delivering a scoring balloon catheter through the vasculature to the lesion, wherein the scoring balloon catheter includes a scoring balloon, a distal control balloon, a proximal control balloon, and a scoring element coupled at a proximal end thereof to the proximal control balloon and at a distal end thereof to the distal control balloon;
positioning the scoring balloon catheter such that the scoring balloon is positioned within the lesion;
inflating the proximal and distal control balloons such that the scoring element becomes taut, wherein the scoring balloon is uninflated and not in contact with the scoring element; and
after inflating the proximal and distal control balloons, inflating the scoring balloon to contact the scoring element and force the scoring element radially outward relative of the longitudinal axis of the scoring balloon catheter such that the scoring element engages the lesion.

15. The method of claim 14, wherein the scoring element is parallel to the longitudinal axis of the scoring balloon catheter.

16. The method of claim 14, wherein the scoring balloon is semi-compliant.

17. The method of claim 14, wherein the scoring balloon is non-compliant.

18. The method of claim 14, wherein the proximal and distal control balloons are compliant.

19. The method of claim 14, wherein the scoring element comprises a plurality of scoring elements.

* * * * *